United States Patent
Kim

(10) Patent No.: US 8,360,954 B2
(45) Date of Patent: Jan. 29, 2013

(54) APPARATUS FOR EXAMINING AND CURING URINARY INCONTINENCE, AND FOR EXERCISING BIO-FEEDBACK OF WOMEN VAGINA MUSCLES

(75) Inventor: Kyungil Kim, Busan (KR)

(73) Assignee: Apimeds, Inc., Gyeonggi (KR)

( * ) Notice: Subject to any disclaimer, the term of this patent is extended or adjusted under 35 U.S.C. 154(b) by 1317 days.

(21) Appl. No.: 11/795,882

(22) PCT Filed: Jun. 30, 2006

(86) PCT No.: PCT/KR2006/002554
§ 371 (c)(1),
(2), (4) Date: Jul. 24, 2007

(87) PCT Pub. No.: WO2007/011118
PCT Pub. Date: Jan. 25, 2007

(65) Prior Publication Data
US 2008/0139876 A1 Jun. 12, 2008

(30) Foreign Application Priority Data
Jul. 19, 2005 (KR) .......................... 10-2005-0065448

(51) Int. Cl.
*A61F 2/00* (2006.01)
(52) U.S. Cl. ............................ 600/29; 600/591; 482/113
(58) Field of Classification Search .................. 600/29, 600/31, 591; 482/113
See application file for complete search history.

(56) References Cited

U.S. PATENT DOCUMENTS

| 3,388,701 | A * | 6/1968 | Breiling et al. ................ 601/150 |
| 5,733,230 | A * | 3/1998 | Sawchuck et al. ............. 482/111 |
| 6,217,529 | B1 | 4/2001 | Wax et al. |
| 6,905,471 | B2 | 6/2005 | Leivseth et al. |
| 2003/0220589 | A1 * | 11/2003 | Leivseth et al. ................ 600/591 |
| 2005/0049509 | A1 * | 3/2005 | Mansour et al. ............... 600/476 |

* cited by examiner

Primary Examiner — Charles A Marmor, II
Assistant Examiner — Carrie R Dorna
(74) Attorney, Agent, or Firm — The Webb Law Firm

(57) ABSTRACT

An apparatus for examining and curing urinary incontinence and exercising the pelvic floor muscles and vaginal muscles using bio-feedback including a controller main body, a probe, and a bio-feedback device. The probe includes: an insert frame extending in a longitudinal direction thereof; an insert expansion part surrounding adjacent to a front end of the insert frame and expandable therearound; an air supply path connected to the interior of the insert expansion part to supply air; a handle engaged with the insert frame; a fixing means for fixing the insert expansion part to the insert frame or the handle; a valve installed at the air supply path; and a PTC ceramic heater and a vibration motor installed at the insert frame. An elastic member includes a magnet, an insertion depth adjustment part, and leg support parts installed at the insertion depth adjustment part. The bio-feedback device includes a sound generating means, and an image display means. The main body includes a controller for controlling each component, a motorized air pump, an air flow detection sensor, a pressure detection sensor, a spring air cylinder, a solenoid air injection valve, an air tank, etc. Therefore, it is possible for a user to readily perform examination and treatment of urinary incontinence and pelvic floor muscle (vagina muscle) reinforcement exercise using bio-feedback.

17 Claims, 16 Drawing Sheets

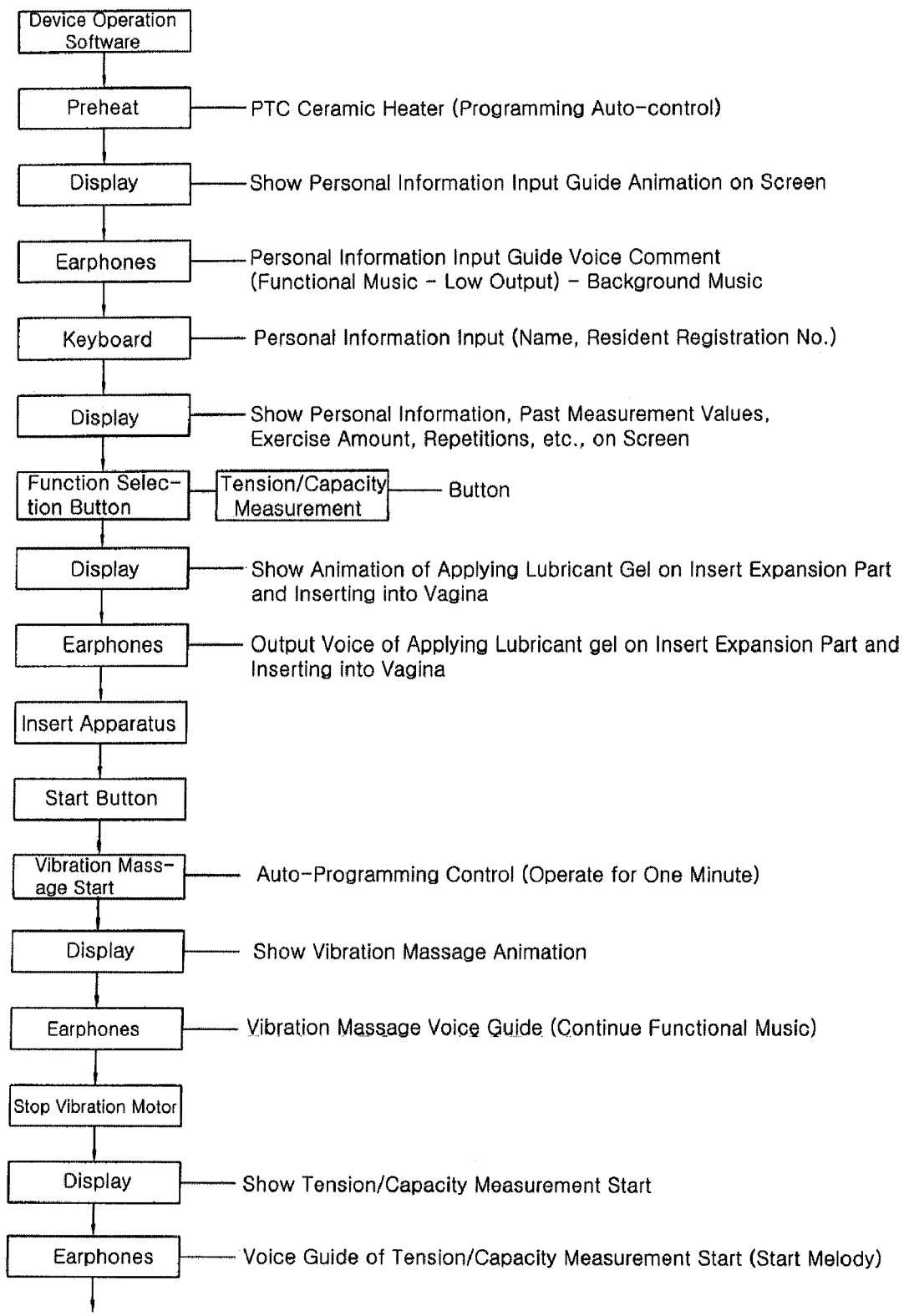
FIG 7-A

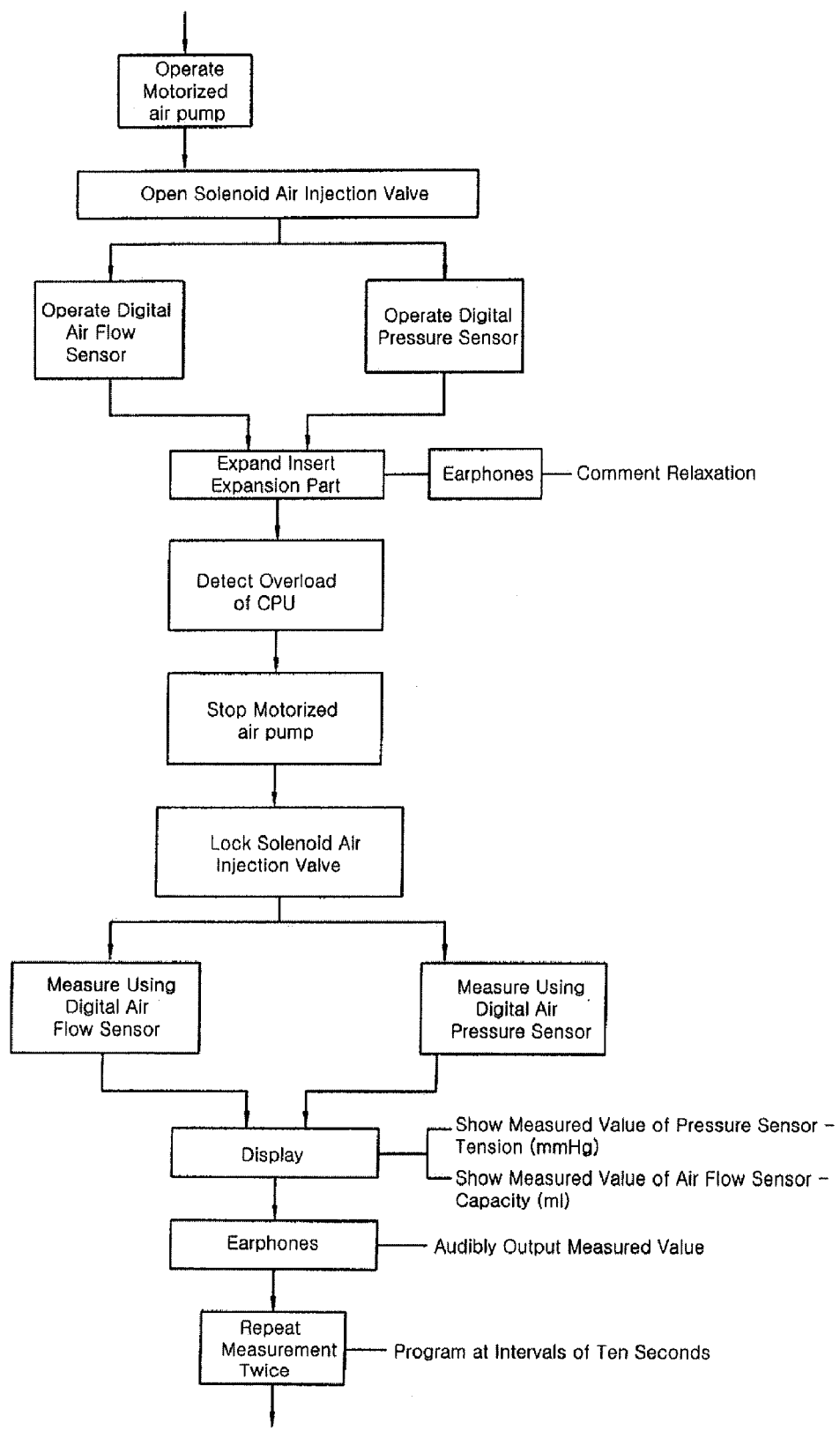
FIG 7-B

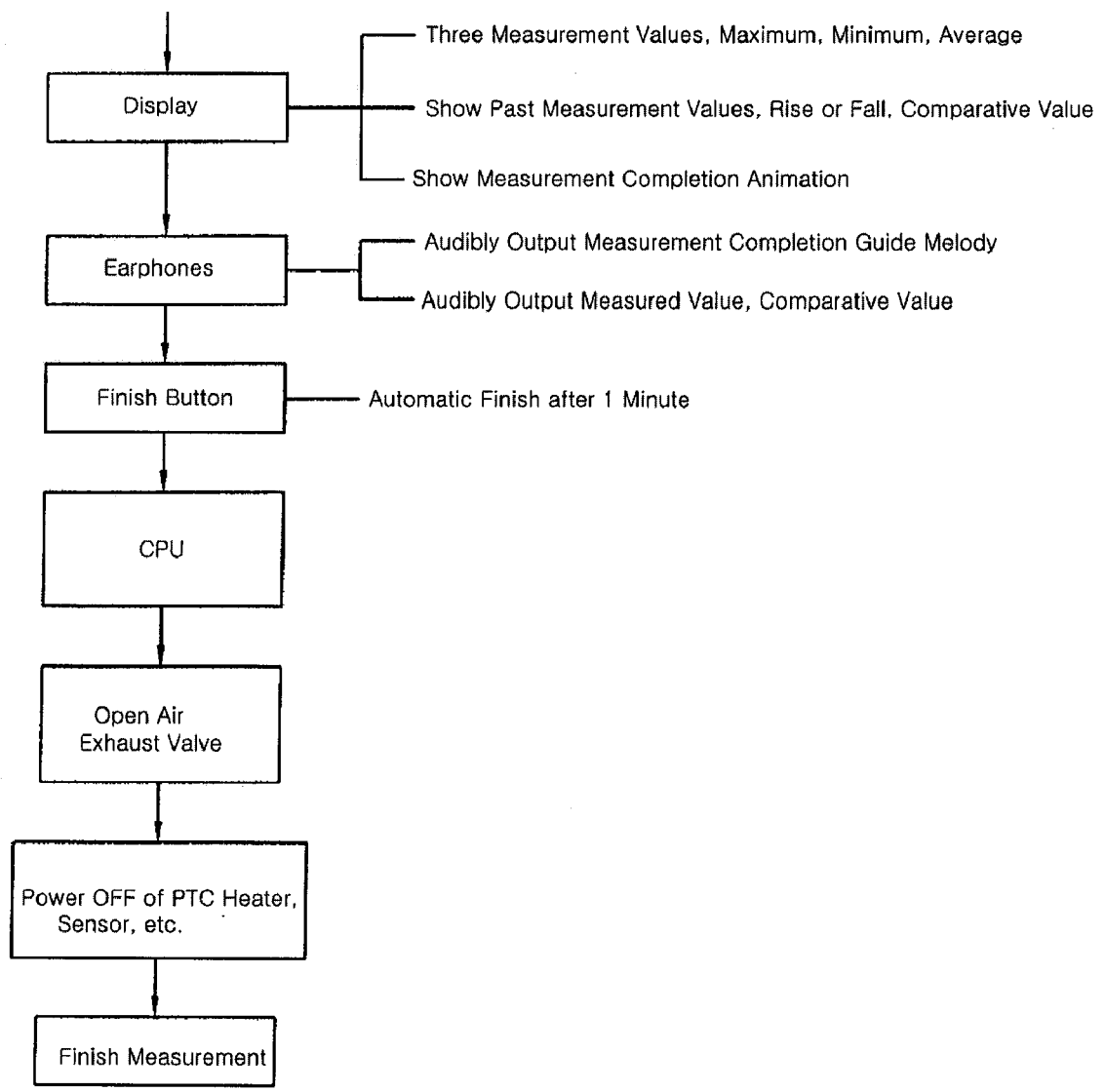
FIG 7-C

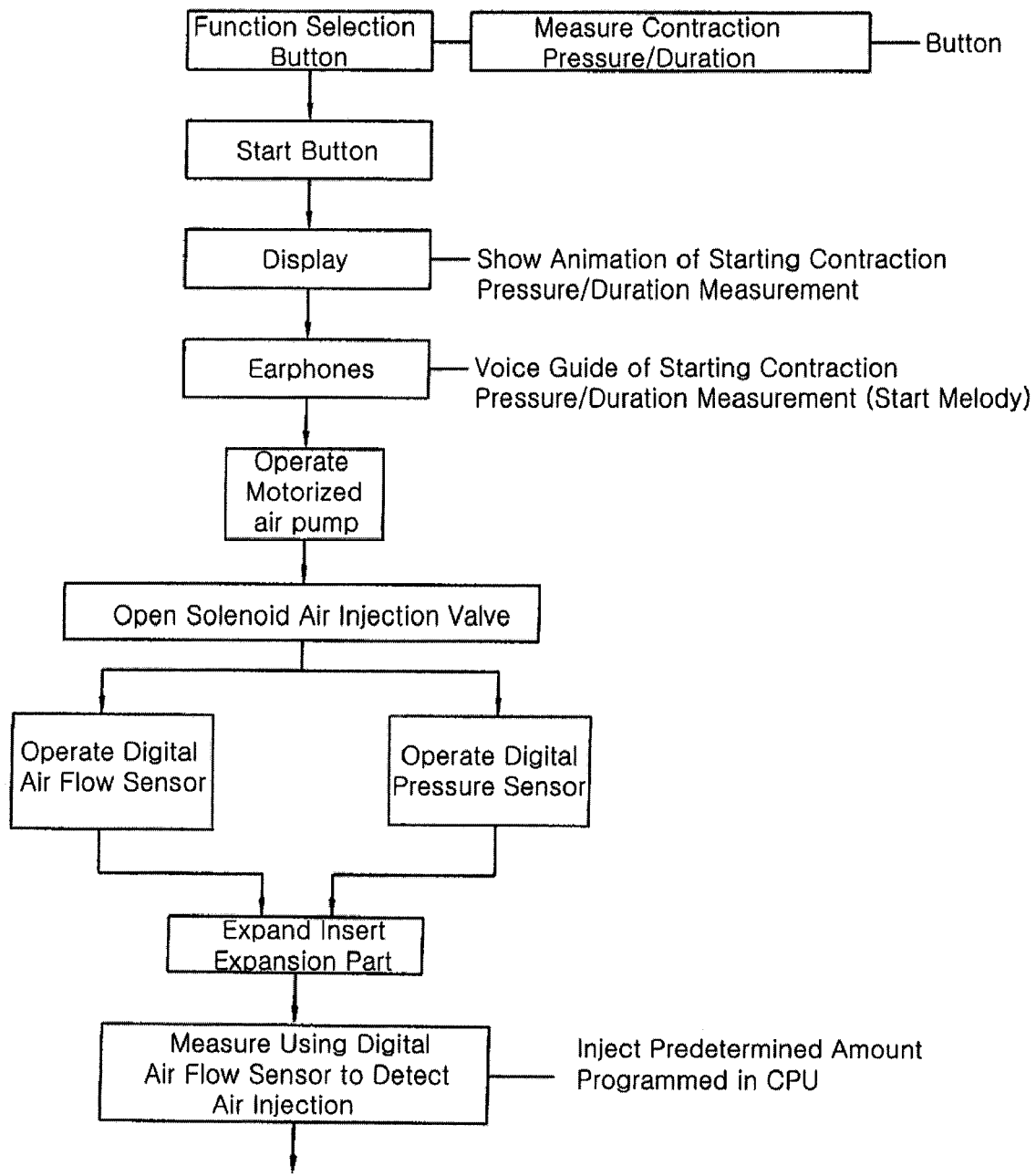
FIG 8-A

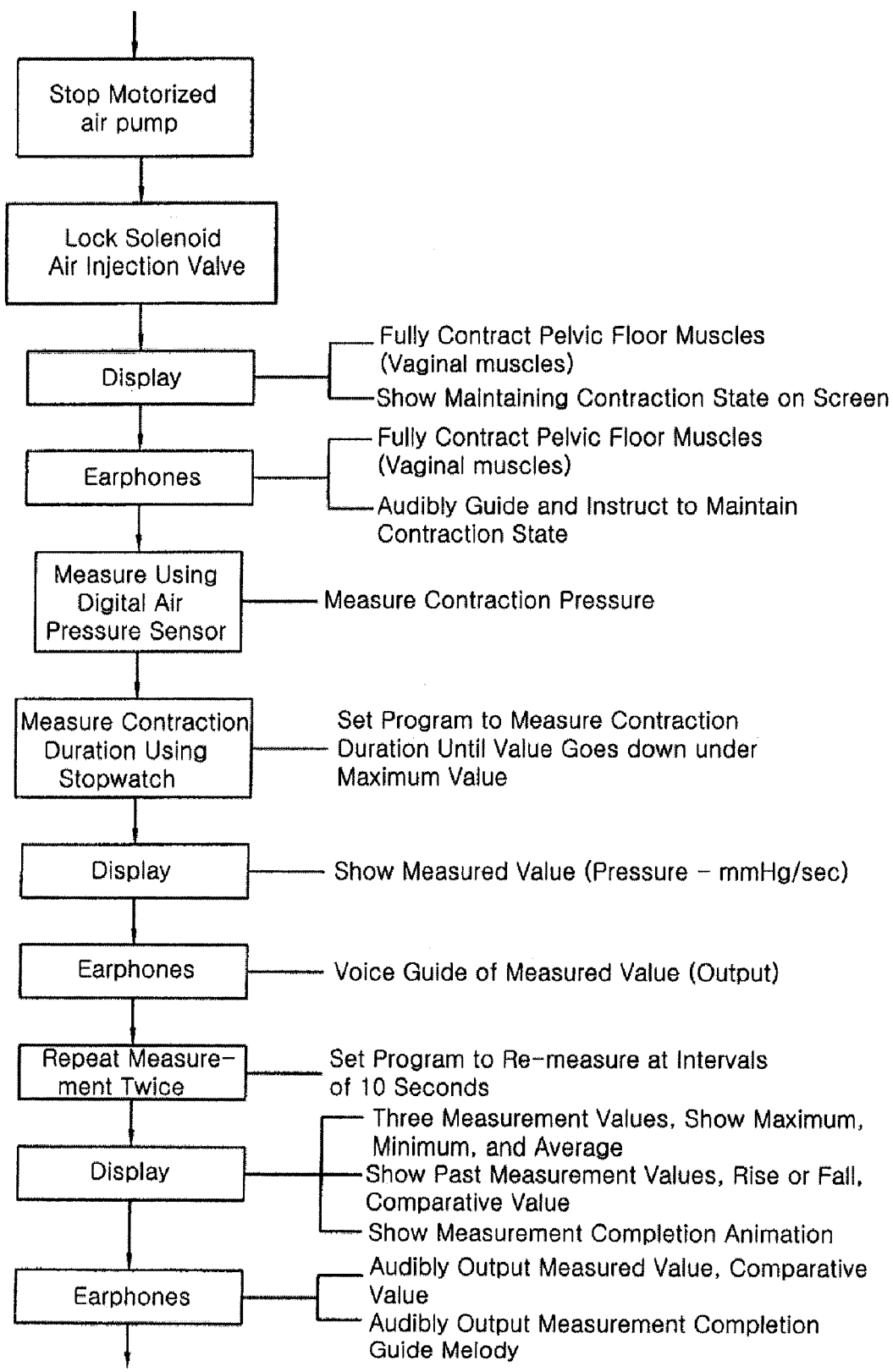
FIG 8-B

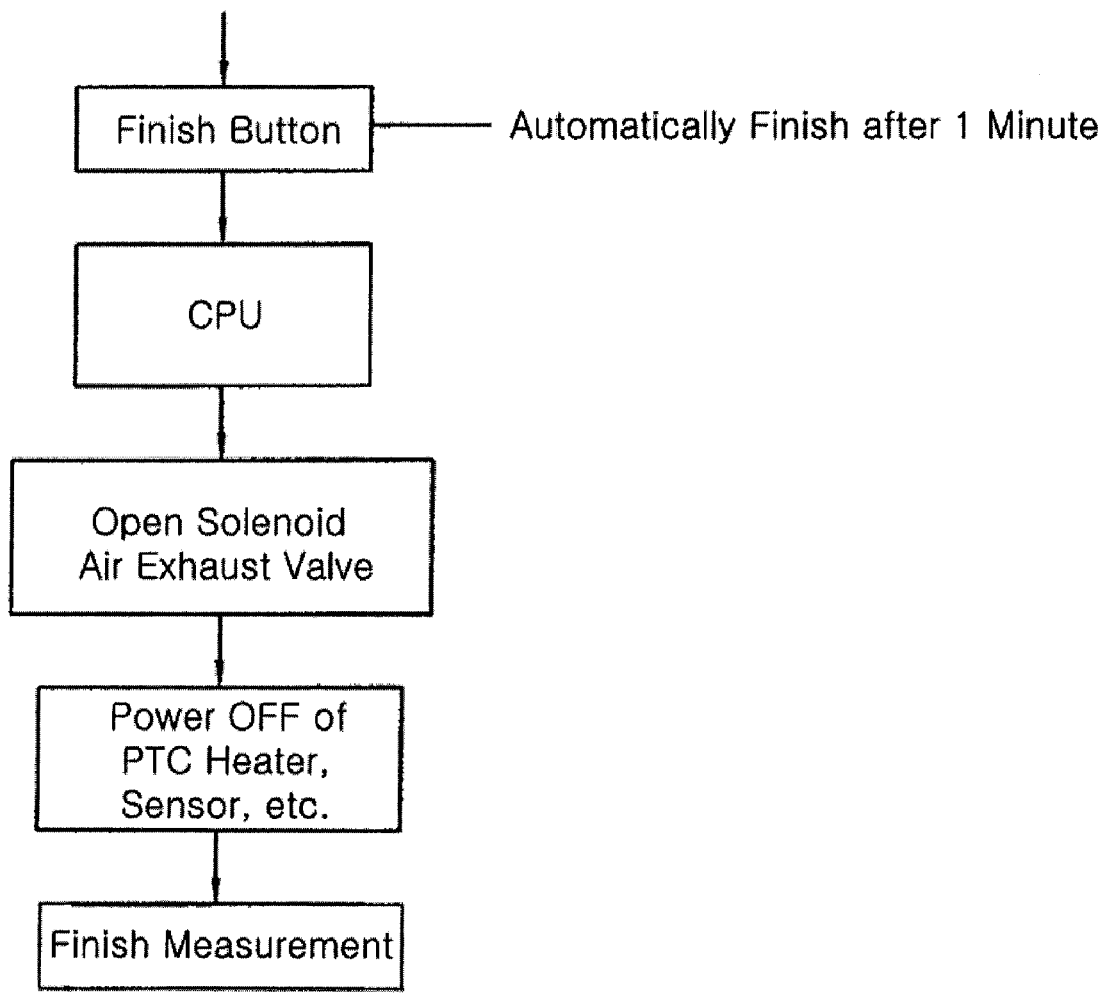
FIG 8-C

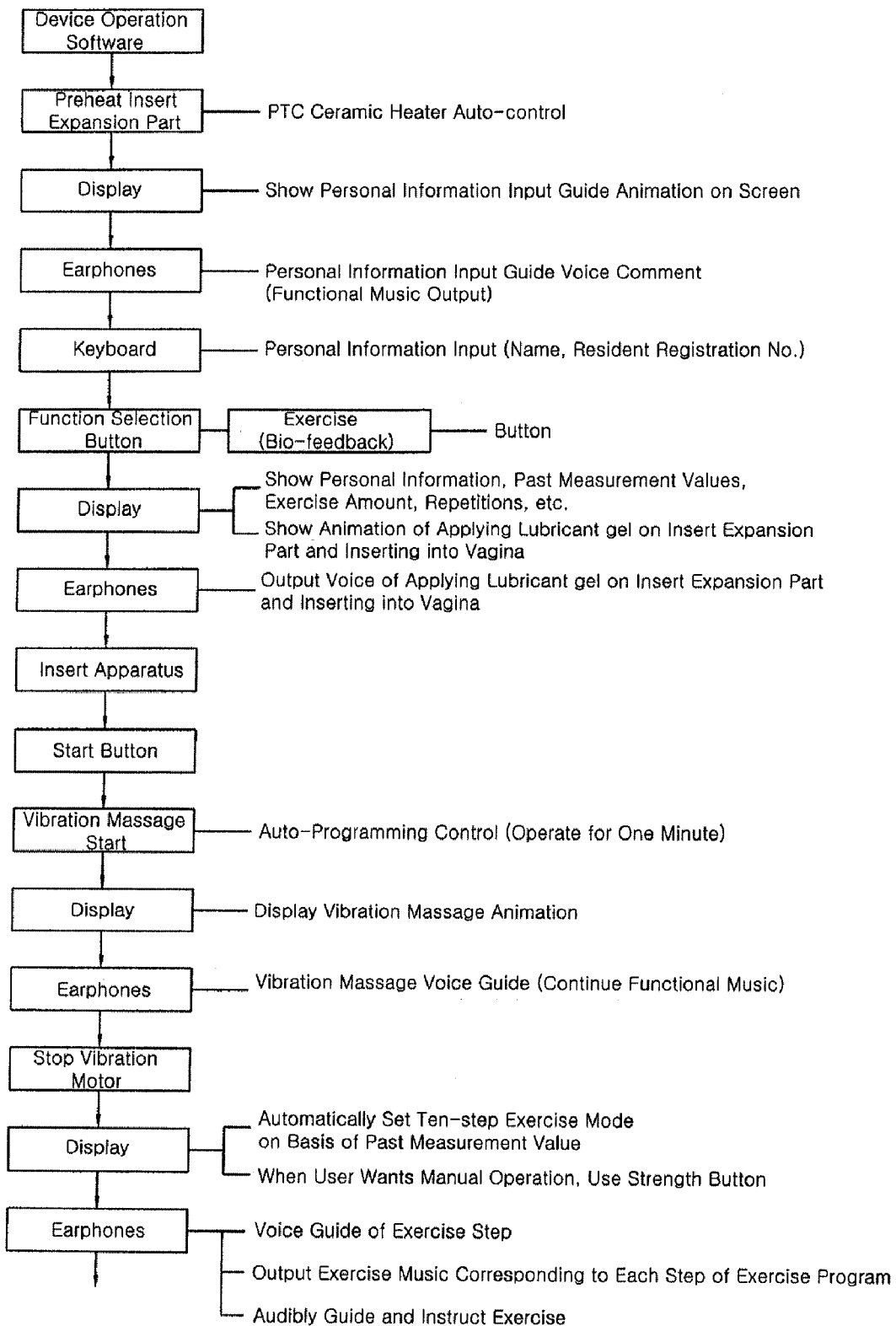
FIG 9-A

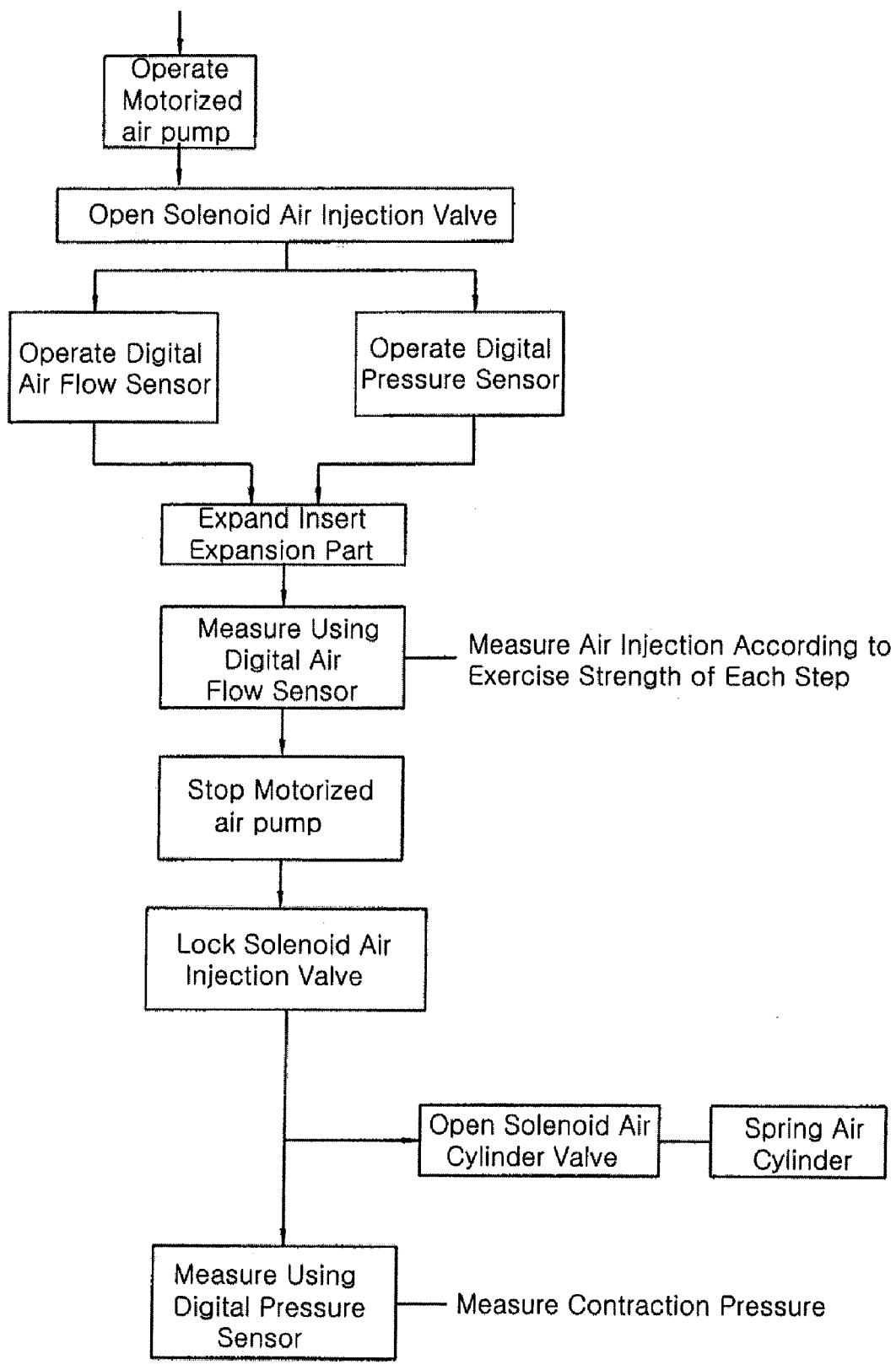
FIG 9-B

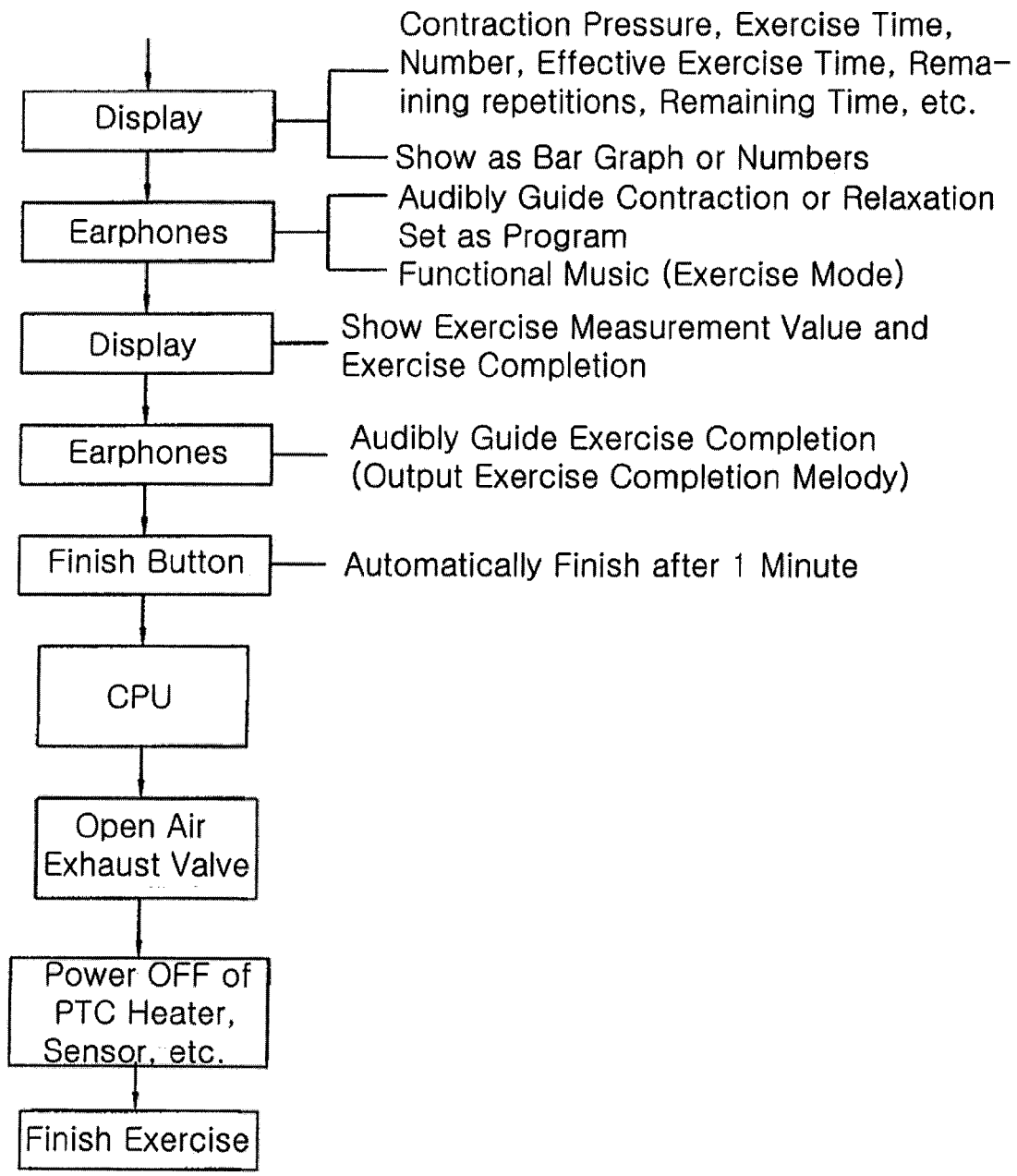
FIG 9-C

APPARATUS FOR EXAMINING AND CURING URINARY INCONTINENCE, AND FOR EXERCISING BIO-FEEDBACK OF WOMEN VAGINA MUSCLES

TECHNICAL FIELD

The present invention relates to an apparatus for examining and curing urinary incontinence and exercising the pelvic floor muscles and vaginal muscles using bio-feedback, and more particularly, to an apparatus capable of allowing a user to personally examine and cure urinary incontinence by herself, and scientifically and accurately strengthening the pelvic floor muscles and vaginal muscles by incorporating a function of using bio-feedback.

BACKGROUND ART

Generally, urinary incontinence is defined as involuntary, spontaneous urination resulting from pressure in the bladder exceeding the resistance provided by weak bladder and sphincter muscle contraction. Urinary incontinence can be a serious problem to social activity and hygiene.

Urinary incontinence may be classified as urge incontinence, stress incontinence, or mixed stress and urge incontinence.

Urge incontinence is involuntary urination resulting from weak or unstable urinary muscles which are insufficient to block the flow of urine when the urge to urinate arises.

Stress incontinence is defined as urination of less than 50 ml when stressful activity that abruptly increases pressure in the abdomen is performed, due to laxity in the urethral ligament, bulbocavernous, perineal, and anal sphincter muscles. The stressful activity may include various activities such as coughing, sneezing, laughing, weight-lifting, running, nose-blowing, intensive exercise, impatience, excitement, stair climbing, abruptly standing-up, and so on.

Mixed stress and urge incontinence results from combination of pressure to the abdomen and laxity of the urinary muscles.

Generally, women are more prone to urinary incontinence than men. Therefore, in today's society, where the participation of women in public affairs and the proportion of senior citizens in the population have abruptly increased, mental, social, and economic damage resulting from urinary incontinence can be very serious. First, with regard to economic damage, a report published in the United States in 1989 reads that the cost of managing urinary incontinence is more than 10 billion US dollars, which is more than is spent on treating AIDS patients.

In addition, urinary incontinence causes the vulva to be always wet, which can lead to skin problems and infection. Further, anxiety, tension, and embarrassment due to odor complicate personal relationships and social activity, which can hurt self-confidence, give a sense of alienation, and even lead to psychological disorders such as depression.

Moreover, excessive expansion of the pelvis during pregnancy and delivery weakens the pelvic muscles (or vaginal muscles) and causes urinary incontinence as well as sexual dysfunction. In a survey, 90% of respondents reported that they have avoided sex at least one time because of urinary incontinence. In particular, 80% of female respondents with serious incontinence avoided sex at all times. Urinary incontinence is a serious condition making it difficult to carry on a sexual relationship as well as causing inconvenience in daily living.

An examination for urinary incontinence may include, for example, a medical examination by interview, a question paper, a uroflowmetric test, a residual urine examination, a urodynamic examination, a crystoscopic examination, X-ray and ultrasonic examination, keeping a urination diary, feminine pad examination, application of a perineometer, and so on. The perineometer is classified as a manual (pump) type or an electronic type. Hospital and university research centers mainly use perineometers to measure pressure and duration of contraction of the pelvic floor muscles in order to evaluate urinary incontinence and the effects of exercise for enhancing the pelvic floor muscles (Kegel exercise). However, since the examination device such as the perineometer is specialized equipment, it is very difficult for a patient to use personally.

Medical treatment of urinary incontinence may include, for example, medicinal therapy, surgical operation, and non-surgical operation.

Medicinal therapy uses medicines such as anticholingeric, a smooth muscle relaxant, tricyclic antidepressant (TCA), and so on. Surgery may include, for example, a sling operation, a Birch's operation, a tension free vaginal tape (TVT) operation, a collagen injection operation, a balloon dilatation operation, and so on.

Non-surgical operation may be classified as either physical therapy or behavior therapy. The physical therapy may include, for example, transcutaneous electrical nerve stimulation (TENS), magnetic field treatment, vaginal cone treatment, thermotherapy, magnetic treatment, feedback using the perineometer, and so on.

TENS is a method of enhancing passive muscle power by applying electric stimulus to the pelvic floor muscles, and magnetic field treatment is a method of passively contracting the pelvic floor muscles using a magnetic field.

The behavior therapy may include, for example, bladder training, Kegel exercise, bio-feedback, and so on.

Bladder training is a method of training the body to urinate at certain times, and Kegel exercise, contrived by Arnold Kegel in 1948, is a widely used method of enhancing the functionality and strength of the pelvic floor muscles by periodically contracting the muscles. Since the pelvic floor muscles (vaginal muscles) are not usually used, it is important to exercise an isolated part of the pelvic floor muscles. However, when the pelvic floor muscles are exercised, the abdominal muscles and the hip muscles are also used, thereby increasing pressure in the abdomen which may aggravate urinary incontinence.

Bio-feedback is a tool for performing physiological self-adjustment, a type of behavior treatment based on the theory of "learning through reinforcement" proposed by B. F. Skinner. A bio-feedback apparatus detects the biological reaction of a patient and converts it into a visible, audible, and/or otherwise sensible signal such that the patient can then see, hear, and/or sense the signal to assist in self-treatment.

DISCLOSURE OF THE INVENTION

Technical Problem

In order to solve the foregoing and/or other problems, it is an aspect of the present invention to provide an apparatus for examining and curing urinary incontinence and exercising the pelvic floor muscles and vaginal muscles using bio-feedback, enabling a patient to measure or test functions of her own pelvic floor muscles and vaginal muscles to examine urinary incontinence symptoms and muscle activation degree, selectively adapt physical therapy and behavior therapy to readily treat urinary incontinence, and exercise using bio-feedback to strengthen the pelvic floor muscles (vaginal muscles).

Technical Solution

One aspect of the present invention provides an apparatus for examining and curing urinary incontinence and exercising the pelvic floor muscles and vaginal muscles using bio-feedback, including: an insert expansion part; an insert frame, a portion of which is accommodated in the insert expansion part, extending in its longitudinal direction; a fixing means for fixing the insert expansion part to the insert frame; an air supply source connected to the insert expansion part and supplying air thereinto; an air supply path disposed between the air supply source and the insert expansion part; and a valve installed at the air supply path.

The air supply path may include a spring air cylinder connected thereto, and a controller for controlling the spring air cylinder.

The insert expansion part or the air supply path may include a pressure detection sensor, a controller for receiving a signal from the pressure detection sensor and processing the signal, and an expression part connected to the controller.

In addition, the air supply path may include an air flow detection sensor, a controller for receiving a signal from the air flow detection sensor and processing the signal, and an expression part connected to the controller.

Another aspect of the present invention provides an apparatus for examining and curing urinary incontinence and exercising the pelvic floor muscles and vaginal muscles using bio-feedback including: an insert expansion part; an insert frame, a portion of which is accommodated in the insert expansion part, extending in its longitudinal direction; a fixing means for fixing the insert expansion part to the insert frame; an air supply source connected to the insert expansion part and supplying air thereinto; an air supply path disposed between the air supply source and the insert expansion part; a valve installed at the air supply path; a pressure detection sensor installed at the insert expansion part or the air supply path; an air flow detection sensor installed at the air supply path; a controller connected to the valve, the pressure detection sensor, and the air flow detection sensor; and an expression part connected to the controller.

The controller may further include a data storage device.

In addition, the expression part may be a sound generating means or an image display means.

Further, the insert expansion part may be formed of an elastic member containing filler.

Furthermore, the elastic member may be formed of rubber including a silicon rubber.

In addition, front and rear ends of the elastic member of the insert expansion part may have a larger thickness than an intermediate part.

Further, the filler may be formed of at least one selected from the group consisting of tourmaline, jade, and elvan powder, and may be gelatinous.

When viewed from the front, the insert expansion part may have an aspect ratio of 1:1.2~1:2.5 on expansion.

In addition, when viewed from the front, the insert expansion part may have a projection part formed at its upper part.

Further, the insert expansion part may have an expansion support piece installed at its front end to be securely engaged with the insert frame.

The insert expansion part may have a fixing piece extending from its rear end.

The insert frame may have a streamlined insertion guide piece in contact with the insert expansion part at its front end.

The insert frame may have at least one selected from a PTC ceramic motor and a vibration motor.

In addition, the elastic member may have a magnet disposed therein.

Meanwhile, the insert frame, disposed outside the insert expansion part, may have an insertion depth adjustment part movable in a longitudinal direction thereof.

In this case, the insertion depth adjustment part may include an insertion adjustment button.

In addition, the insertion depth adjustment part may include leg support parts extending in lateral directions thereof.

Further, the insert frame, disposed outside the insert expansion part, may include a handle.

The controller may include a stopwatch connected thereto.

BRIEF DESCRIPTION OF THE DRAWINGS

These and/or other aspects and advantages of the present invention will become apparent and more readily appreciated from the following description of exemplary embodiments of the invention, taken in conjunction with the accompanying drawings of which:

FIGS. 7A to 7C are flowcharts showing an operational example for measuring a tension force of the pelvic floor muscles (vaginal muscles) and an internal volume of the vagina using an apparatus for examining and curing urinary incontinence and exercising the pelvic floor muscles and vaginal muscles using bio-feedback, in accordance with an exemplary embodiment of the present invention FIGS. 8A to 8C are flowcharts showing an operational example for measuring a pressure and duration of contraction of the pelvic floor muscles (vaginal muscles) using an apparatus for examining and curing urinary incontinence and exercising the pelvic floor muscles and vaginal muscles using bio-feedback, in accordance with an exemplary embodiment of the present invention FIGS. 9A to 9C are flowcharts showing an operational example of exercising using bio-feedback for reinforcement of the pelvic floor muscles (vaginal muscles) using an apparatus for examining and curing urinary incontinence and exercising the pelvic floor muscles and vaginal muscles using bio-feedback, in accordance with an exemplary embodiment of the present invention

MODES OF THE INVENTION

Figure 1:
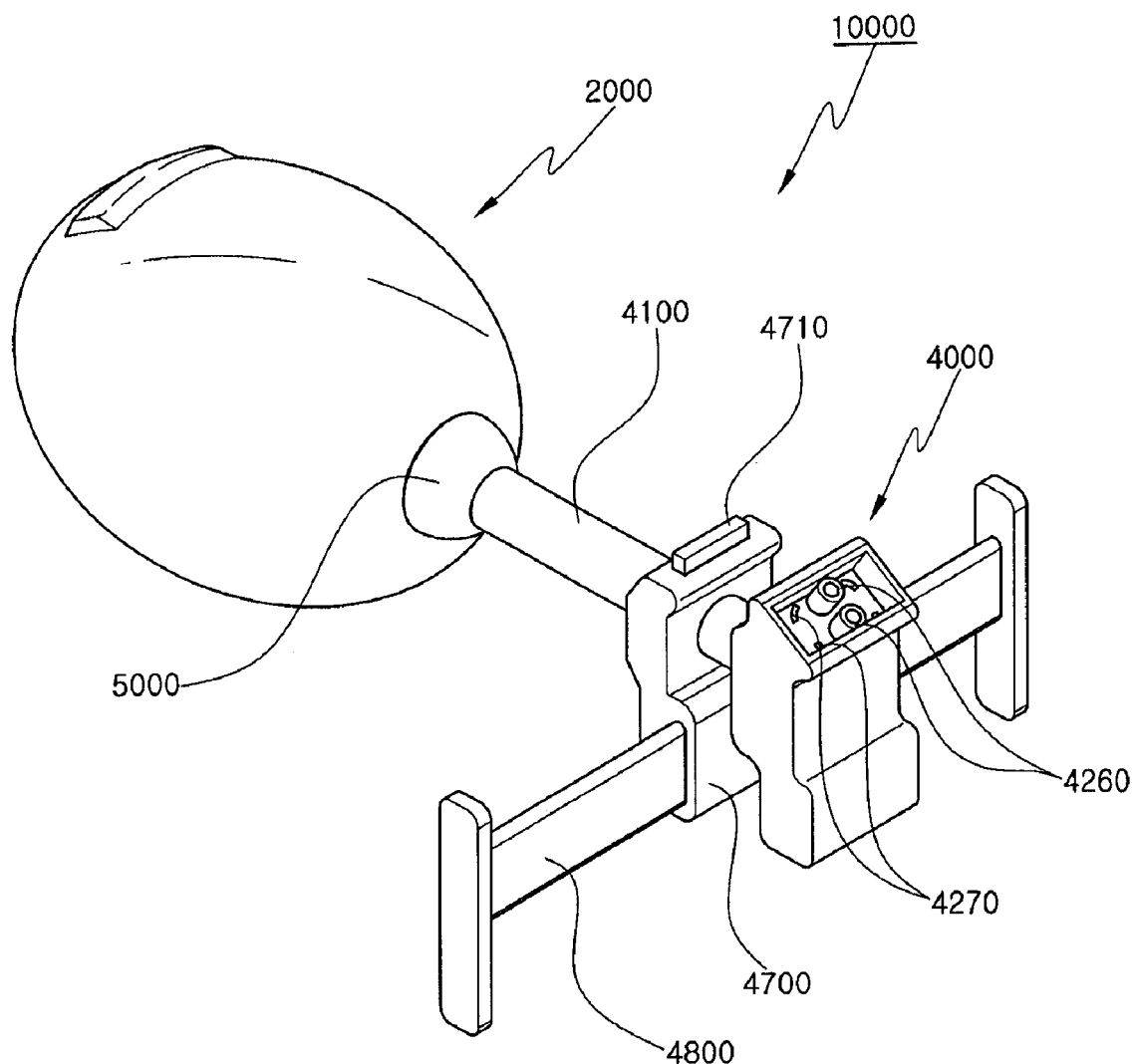
FIG. 1 is a perspective view of an apparatus for examining and curing urinary incontinence and exercising the pelvic floor muscles and vaginal muscles using bio-feedback, in accordance with an exemplary embodiment of the present invention

Exemplary embodiments of the present invention will now be described in detail with reference to FIGS. 1 to 10, throughout which like reference numerals refer to like elements.

As shown, an apparatus for examining and curing urinary incontinence and exercising the pelvic floor muscles and vaginal muscles using bio-feedback, in accordance with an exemplary embodiment of the present invention, includes a probe 10000, and peripheral devices such as a main body box, a bio-feedback device, and so on. The probe 10000 includes an insert expansion part 2000, an insert frame 1000, a portion of which is accommodated in the insert expansion part 2000, extending in its longitudinal direction; a fixing means 5000 for fixing the insert expansion part 2000 to the insert frame 1000; an air supply source (not shown) connected to the insert expansion part 2000 and supplying air thereinto; an air supply path 3000 disposed between the air supply source and the insert expansion part 2000; and a valve installed at the air supply path 3000.

First, the insert frame 1000 functions as a skeleton disposed in the insert expansion part 2000, which is actually inserted into a women's vagina. For this purpose, the insert frame 1000 includes an insertion guide piece 1500 having a convex and smooth front surface at its front end such that the insert frame 1000 can be smoothly inserted into the vagina. The insertion guide piece 1500 also functions to securely support the insert expansion part 2000 in a longitudinal direction thereof. In addition, the insert frame 1000 has a passageway 1900 for supplying air into the insert expansion part 2000.

The insert frame 1000 may be formed of a medical silicon, a medical PVC, or a medical metal.

Figure 2:
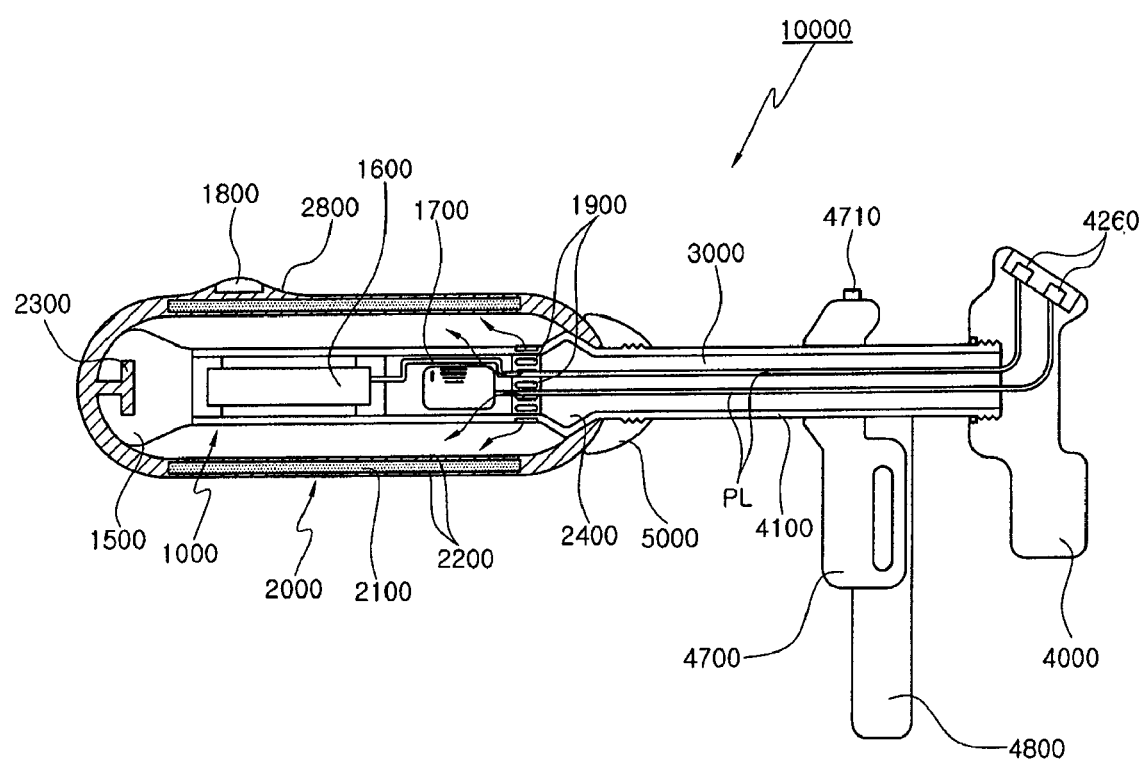
FIG. 2 is a longitudinal cross-sectional view of an apparatus for examining and curing urinary incontinence and exercising the pelvic floor muscles and vaginal muscles using bio-feedback, in accordance with an exemplary embodiment of the present invention

In addition, as shown in FIG. 2, the insert frame 1000 includes a heater 1600 and a vibration motor 1700.

The heater 1600 may be a positive temperature coefficient (PTC) ceramic heater. This is because the PTC ceramic heater arrives at a maximum temperature within a short time, has good corrosion-resistance and durability, has a semi-permanent lifespan, and does not overheat. In addition, a PTC device has temperature self-control characteristics and does not require a separate ON/OFF control function, thereby effectively preventing overheating. Further, it is advantageous for a large quantity of far infrared rays to be emitted together with the heat for thermotherapy.

Of course, a general resistance heater may also be used.

The vibration motor 1700 may be a general vibration motor using an eccentric shaft. The vibration motor massages the pelvic floor muscles (vaginal muscles) before and after the examination (measurement), treatment, and the pelvic floor muscle (vagina muscle) reinforcement exercise (Kegel Exercise), to break muscle fatigue and increase muscle building. In addition, the vibration motor functions as vibration massage treatment of the pelvic floor muscles (vaginal muscles) during the treatment. Further, it is possible to function as a vibrator during the pelvic floor muscle (vagina muscle) reinforcement exercise to perform sense-feedback.

Meanwhile, the insert frame 1000 includes the insert expansion part 2000 expandably installed therearound.

In addition, the insert expansion part 2000 may be formed of at least one layer of elastic member 2200. When at least two layers are used, tension and durability are remarkably increased to enhance safety.

The elastic member 2200 may be formed of a medical rubber or a medical silicon used to make artificial organs (heart, urethra, breast, kidney, etc.) and is harmless to the human body and has no side-effects.

In addition, the elastic member 2200 has front and rear ends that are thicker than an intermediate part such that a smooth surface condition is maintained even when air is not injected and expansion can be uniform with an even pressure distribution.

Further, in the case that the elastic member 2200 is formed of two layers, a filler 2100 may be interposed between the two layers of the elastic member 2200 to improve anti-friction performance and expansibility. The filler 2100, widely used for medical products, may be formed of at least one selected from tourmaline, jade, and elvan powder. That is, only one material may be used, or at least two materials may be used. In the case of mixing at least two materials, there is no particular restriction on the mixing ratio. Moreover, these materials may be gelatinous to increase fluidity.

In addition, the materials are known to emit a large amount of far infrared rays and anions. First, the far infrared rays function to perform thermotherapy, anti-aging treatment, magnetic treatment, drying and wetting, neutralization, resonance, and so on, thereby maintaining and appropriate temperature and moisture level of the body, accelerating discharge of bodily waste, neutralizing odor, and promoting metabolism. Further, the anions activate functions of cells and autonomic nerves to promote functions of endocrine and blood cell production.

Furthermore, the filler 2100 can emit a larger amount of far infrared rays and anions by heat discharged from the PTC ceramic heater 1600.

A medical magnet 1800 may be disposed between the two layers of the elastic member 220 or inside the single elastic member to apply magnetic force to the pelvic floor muscles (vaginal muscles) to perform magnetic treatment for helping blood circulation and soothing pain.

Meanwhile, the insert expansion part 2000 includes an expansion support piece 2300 installed at its front end. The expansion support piece 2300 is hooked to the insert frame to prevent distortion of the insert expansion part 2000 and ensure uniform expansion and contraction during operation.

In addition, the insert expansion part 2000 is fixed to the insert frame 1000 at its rear end through the medium of a fixing piece 2400.

When viewed from the front, the insert expansion part 2000 may have an aspect ratio (width:height) of 1:1.2~2.5 during the expansion. According to the above constitution, it is possible to effectively treat urinary incontinence by structurally supporting or pressing various muscles supporting the sagging bladder, the urethra and the pelvis, and the laterally extended vaginal muscles.

In addition, when viewed from the front, a semi-spherical projection 2800 formed at an upper part of the insert expansion part 2000 can press the sagging bladder, the urethra, and the vaginal ceiling to treat urinary incontinence physiologically, and support and press the laterally extended vaginal muscles to increase tension and elasticity thereof. The projection 2800 may be disposed at a longitudinal position corresponding to ¼~½ from an upper end of the insert expansion part 2000, and may have a spherical shape with a diameter of about 3~10 mm, but is not limited thereto.

Meanwhile, the air supply path 3000 is connected from the interior of the insert expansion part 2000 to the air supply source (not shown) constituted of an air pump, a high pressure air tank, and so on. A portion of the air supply path 3000 may pass through a portion of the insert frame 1000 or the interior of the handle 4000.

A valve (not shown) for opening/closing the air supply path 3000 is installed at the air supply path 3000. In this case, a solenoid valve may be employed to enable electronic opening/closing using a switch. The air supply pressure may be determined by the operation of the valve to appropriately adjust the interval and strength of the expansion and contraction of the insert expansion part 2000.

In addition, the insert expansion part 2000 may be connected to a pressure distribution apparatus such as the spring air cylinder 3700. Therefore, when the pelvic floor muscle (vagina muscle) reinforcement exercise is performed, it is possible to distribute the pressure of the insert expansion part 2000 such that light exercise can be performed during an exercise mode of each step. The spring air cylinder is formed of a cylindrical PVC member and has a piston installed therein and a spring installed at a lower part thereof. Installation of at least two springs enables adjustment to various strengths.

Figure 10:
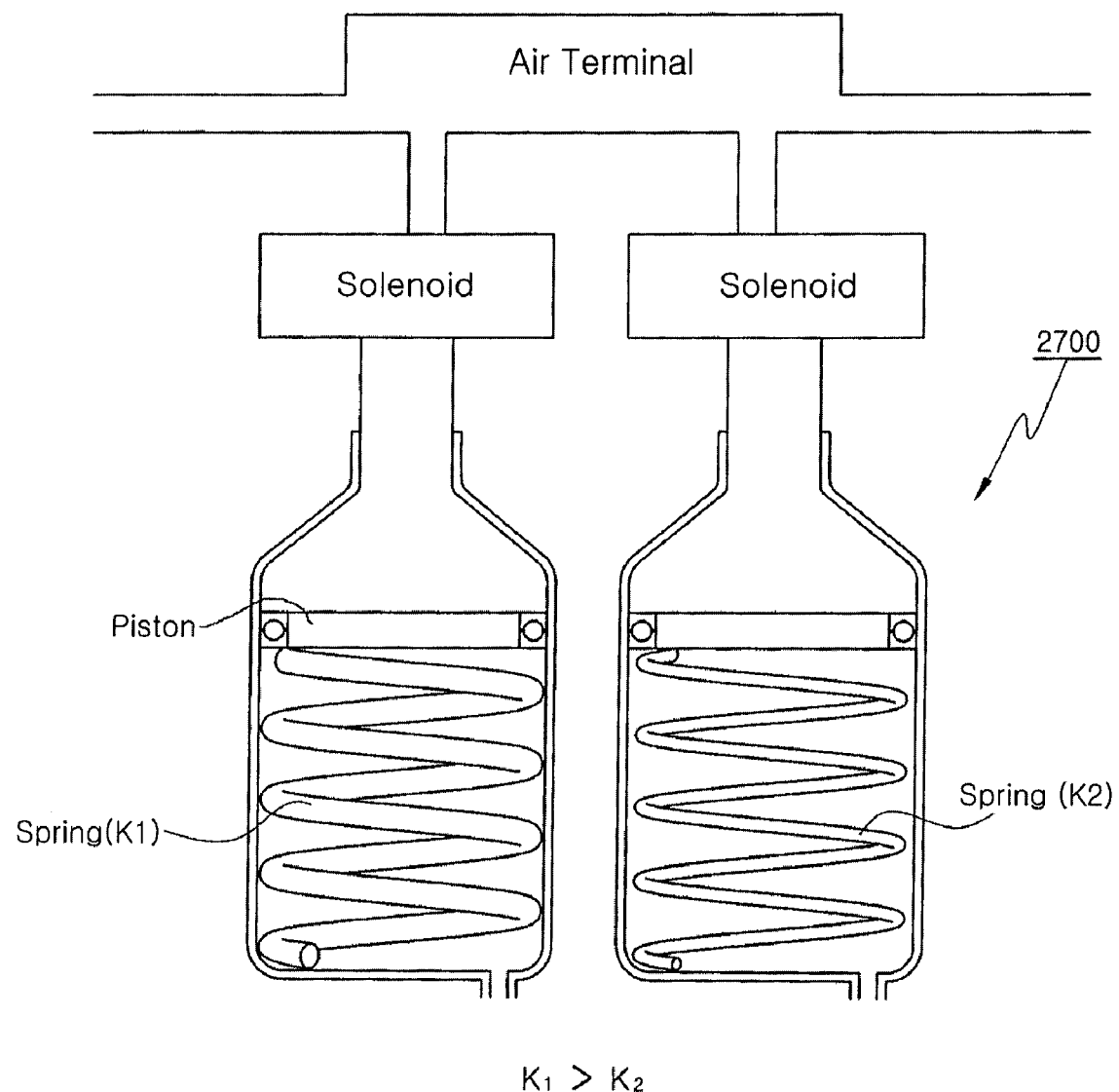
FIG. 10 is a schematic view of a spring air cylinder of an apparatus for examining and curing urinary incontinence and exercising the pelvic floor muscles and vaginal muscles using bio-feedback, in accordance with an exemplary embodiment of the present invention.

The structure of the solenoid air cylinder is schematically illustrated in FIG. 10.

As shown in FIG. 10, in order to distribute the pressure of the air introduced into the insert expansion part 2000, the spring and the piston are engaged with each other in the cylinder. More specifically, pressure is selectively applied to the corresponding piston on the basis of a strong or soft mode to expand its space and distribute the pressure.

A general hydraulic or pneumatic cylinder may be employed instead of the spring air cylinder.

The air supply path 3000 may include an air flow detection sensor (not shown). The air flow detection sensor measures the flux of air into the insert expansion part 2000 from the motorized air pump to measure the capacity (cc or ml) of the vagina, and measures appropriate air flux injected into the insert expansion part 2000 on the basis of the measurement items, when the tensional force (mmHg), the contraction force (mmHg), and the contraction duration (sec) of the pelvic floor muscles (vaginal muscles) are measured. In addition, even when the pelvic floor muscle (vagina muscle) reinforcement exercise is performed, it is possible to measure an appropriate flux of air into the insert expansion part 2000 according to each step of the exercise strength. The measurement values from the air flow detection sensor are digitalized to be displayed on a separate display device and used to measure the capacity of the vagina.

In addition, a pressure sensor (not shown) is also installed at the insert expansion part 2000 or the air supply path 3000 to measure the tensional force (mmHg) and the contraction pressure (mmHg) of the pelvic floor muscles (vaginal muscles), and measure the contraction pressure (mmHg) even during the pelvic floor muscle (vagina muscle) reinforcement exercise. The measurement values from the pressure detection sensor are digitalized to be displayed on a separate display device and used to measure the tensional force and the contraction force of the pelvic floor muscles (vaginal muscles).

In addition, a stopwatch is installed to measure the contraction duration (sec) of the pelvic floor muscles (vaginal muscles) and control an operation time of the PTC ceramic heater and the vibration motor installed in the probe. Further, the stopwatch functions to control the exercise amount and the exercise speed even while the pelvic floor muscle reinforcement exercise is performed. The measurement time from the stopwatch is digitalized to be displayed on a separate display device.

The insert expansion part 2000 is engaged with the insert frame 1000 at its rear end through the medium of the fixing means 5000. Specifically, the insert frame 1000 has a female-threaded part formed at its surface, and the fixing means 5000 has a male-threaded part, thereby securely assembling together. However, this is merely an example and other conventional coupling means may be applied.

Meanwhile, the insert frame 1000 includes the handle 4000 formed at its rear end. Using the handle 4000, the front end of the insert expansion part 2000 can be readily inserted into and removed from the vagina.

The handle 4000 includes an air supply port 4270 and a power cable connector 4260. Power for the heater 1600, the vibration motor 1700, the air supply valve, etc., can be supplied through the power cable connector 4260. A power supply line PL is connected between the power cable connector 4260 and the above power load devices. In addition, the insertion depth adjustment part 4700 is longitudinally movably installed at the insert frame 1000, exposed to the exterior of the insert expansion part 2000, such that the insertion depth into the vagina of the insert frame 1000 can be adjusted depending on the depth of the vagina and the treatment part.

For this purpose, the insertion depth adjustment part 4700 includes an insertion adjustment button 410. The insertion adjustment button 4710 employs a general spring switch structure such that a tightened state of the insertion depth adjustment part 4700 is released when the button 4710 is pushed to enable them to move freely relative to one another. In addition, a general toggle switch structure for alternately performing fixing and release may be employed.

Further, the insertion depth adjustment part 4700 includes leg support parts 4800 laterally installed thereon. The leg support parts 4800 are movable along a movement guide bar 4100. In addition, the leg support parts 4800 employ a general toggle spring structure, which is alternately pushed down by pushing it and rebounding by re-pushing it. However, the leg support parts 4800 may be directly fixed to the insert frame 1000 extending from the insert expansion part 2000 and exposed to the exterior. Since the leg support parts 4800 are in contact with the body, such as the inside of the thighs, and so on, which may be formed of a soft silicon rubber or a soft PVC.

Figure 3:
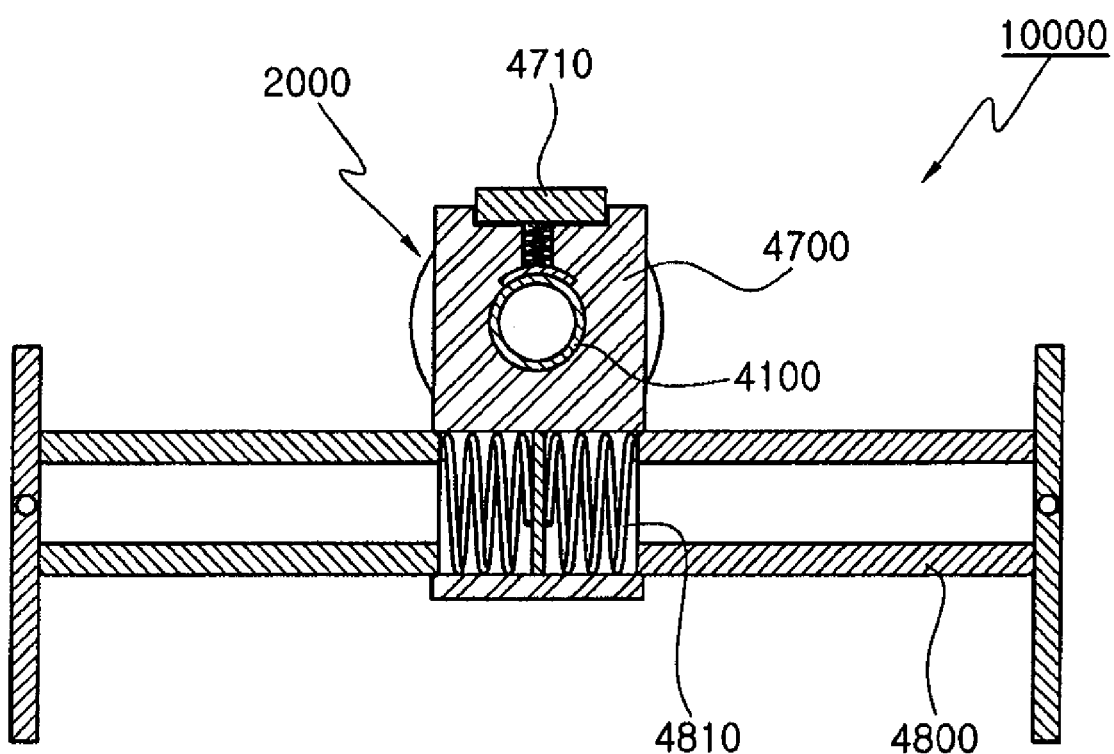
FIG. 3 is a rear view of an apparatus for examining and curing urinary incontinence and exercising the pelvic floor muscles and vaginal muscles using bio-feedback, in accordance with an exemplary embodiment of the present invention

The leg support parts 4800 enable examination, treatment, and the pelvic floor muscle (vaginal muscle) reinforcement exercise in a more stable posture, as well as prevent separation from the body. Moreover, as shown in FIG. 3, the leg support parts 4800 are separately adjusted by the spring 4810 to differently distribute leg force, thereby facilitating its use.

Figure 4:
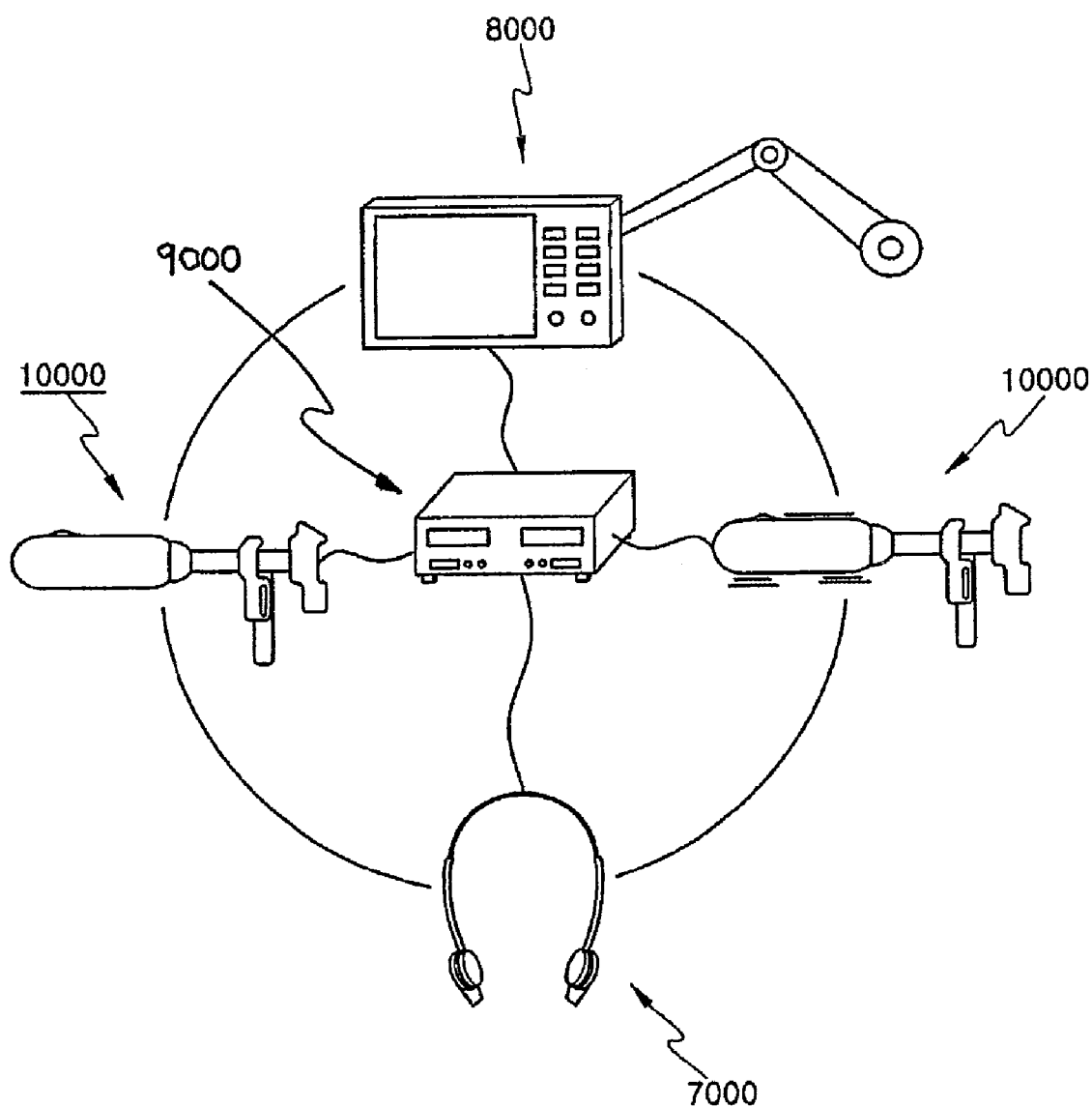
FIG. 4 is a schematic view showing the technical concept of bio-feedback of an apparatus for examining and curing urinary incontinence and exercising the pelvic floor muscles and vaginal muscles using bio-feedback, in accordance with an exemplary embodiment of the present invention

Further, as shown in FIG. 4, the apparatus for examining and curing urinary incontinence and exercising the pelvic floor muscles and vaginal muscles using bio-feedback, in accordance with an exemplary embodiment of the present invention, may further include a sound generating means 7000 and an image display means 8000 such as a liquid crystal display monitor, etc., to perform bio-feedback.

First, a user can adjust her body condition with listening to various instructions from the sound generating means 7000. In addition, it is also possible to perform music therapy using the sound generating means 7000. Music therapy relaxes the user's tensed mind and muscles to accelerate the treatment effect. More specifically, a functional music program installed in the controller may be operated during examination (measurement), treatment, and the pelvic floor muscle (vagina muscle) reinforcement exercise, to output functional music corresponding to each functional item or each step of the condition/symptom, thereby providing music therapy.

Further, the user can directly check various states (tension, contraction pressure, capacity of the vagina, treatment time, exercise time, exercise strength, exercise repetitions, measurement history, etc.) using the display means 8000, thereby performing the examination (measurement) and the pelvic floor muscle (vagina muscle) reinforcement exercise by herself.

Furthermore, the controller 9000 is installed to control the various functions. More specifically, the controller is a major component of the main body required to control each component, the motorized air pump, solenoid, air injection valve, PTC ceramic heater, vibration motor, LCD display as the bio-feedback device, earphones, and operation flow of the examination (measurement), treatment, pelvic floor muscle (vagina muscle) reinforcement exercise, etc. In addition, the controller 9000 functions to store the current and past measurement value, measurement date, the number of measurements, etc., of each examination item, and the current and past treatment step, the number of treatments, accumulated treatment time, etc., of each treatment item, and stores and controls the current and past exercise amount, accumulated exercise time, exercise strength, etc. For this purpose, the controller 9000 may further include a central processing unit (CPU) and a memory device.

Meanwhile, using the above constitution, it is possible to accomplish urinary incontinence examination and treatment and the pelvic floor muscle (vagina muscle) bio-feedback exercise according to a 3-way and 4-channel method. A 3-way and 4-channel system will be described in detail below.

◆ 3-WAY-4CHANNEL SYSTEM
▣ WAY-Self-Test/Measurement
① Pelvic Floor Muscles/Vaginal muscles: Measurement of Muscle Tension
② Measurement of Vagina Capacity
③ Pelvic Floor Muscles/Vaginal muscles: Measurement of Contraction/Resting Pressure
④ Pelvic Floor Muscles/Vaginal muscles: Measurement of Contraction Duration
▣ 2WAY-Self-Treatment/Therapy
① Thermotherapy
② Far infrared/Anion/Magnetic Therapy
③ Vibration Massage Therapy
④ Music Therapy
▣ 3WAY-(Self-Pelvic Floor Muscles/Vaginal muscles Reinforcement Exercise)-BIOFEEDBACK
① Exerciser-Probe
② Visual Feedback-LCD Display
③ Audible Feedback-Headphone
④ Sensory Feedback-Vibration Probe The above functions can be smoothly performed by disposing the following functional buttons at a separate adjustment device installed at a control box, etc. and transmitting the control signal corresponding to operation of the buttons to the apparatus for examining and curing urinary incontinence and exercising the pelvic floor muscles and vaginal muscles using bio-feedback through the controller 9000.
1) Tension/Capacity measurement button
2) Contraction Pressure/Duration Measurement Button
3) Thermotherapy Button
4) Massage Button
5) Bio-feedback Button
6) Display Button
7) Sound Button
8) Vibration Button In addition, FIG. 5 is a block diagram illustrating control and air flow for performing the above functions in an apparatus for examining and curing urinary incontinence and exercising the pelvic floor muscles and vaginal muscles using bio-feedback, in accordance with the present invention.

Figure 5:
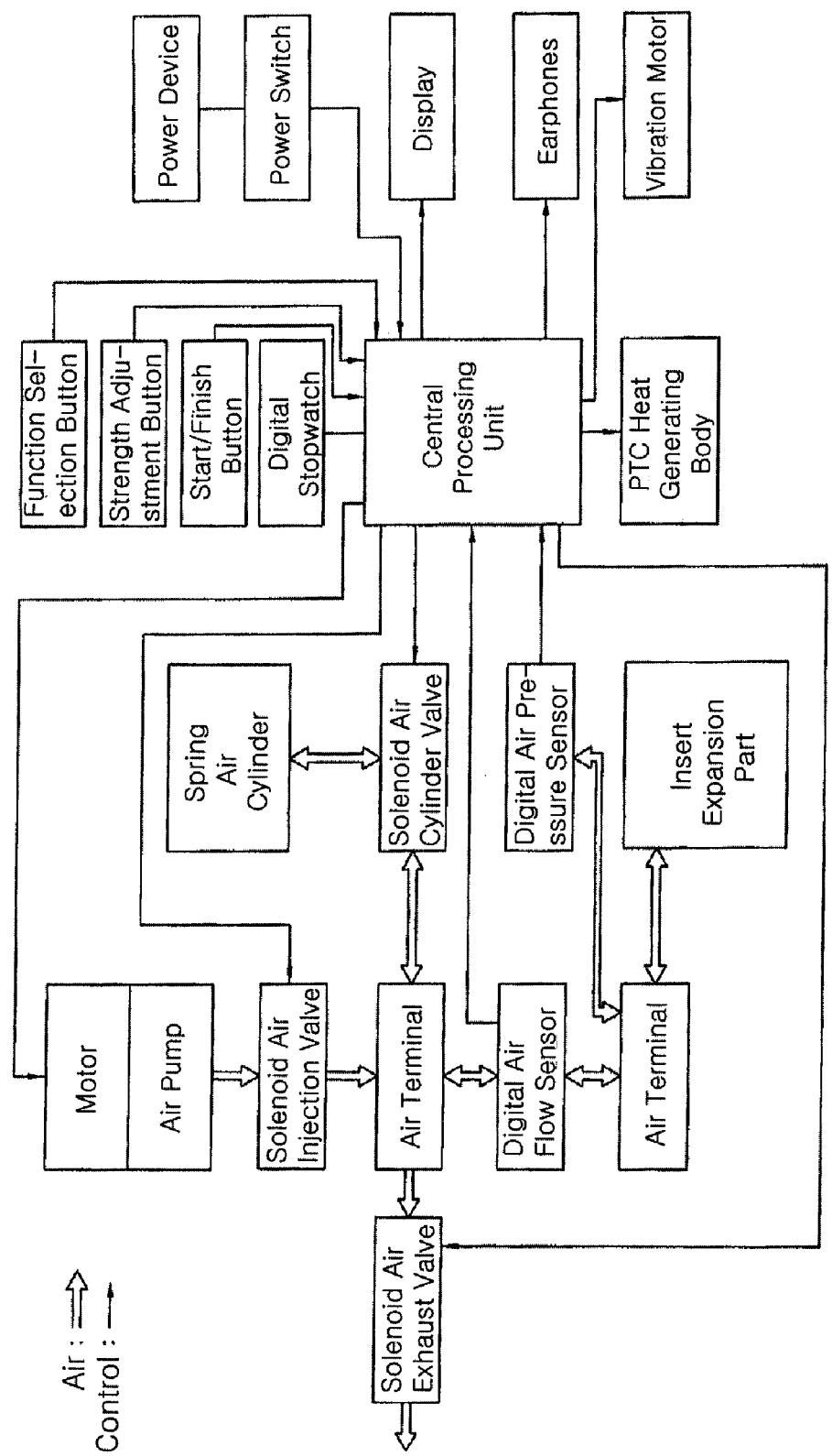
FIG. 5 is a block diagram showing control and air flow of an apparatus for examining and curing urinary incontinence and exercising the pelvic floor muscles and vaginal muscles using bio-feedback, in accordance with an exemplary embodiment of the present invention
Figure 6:
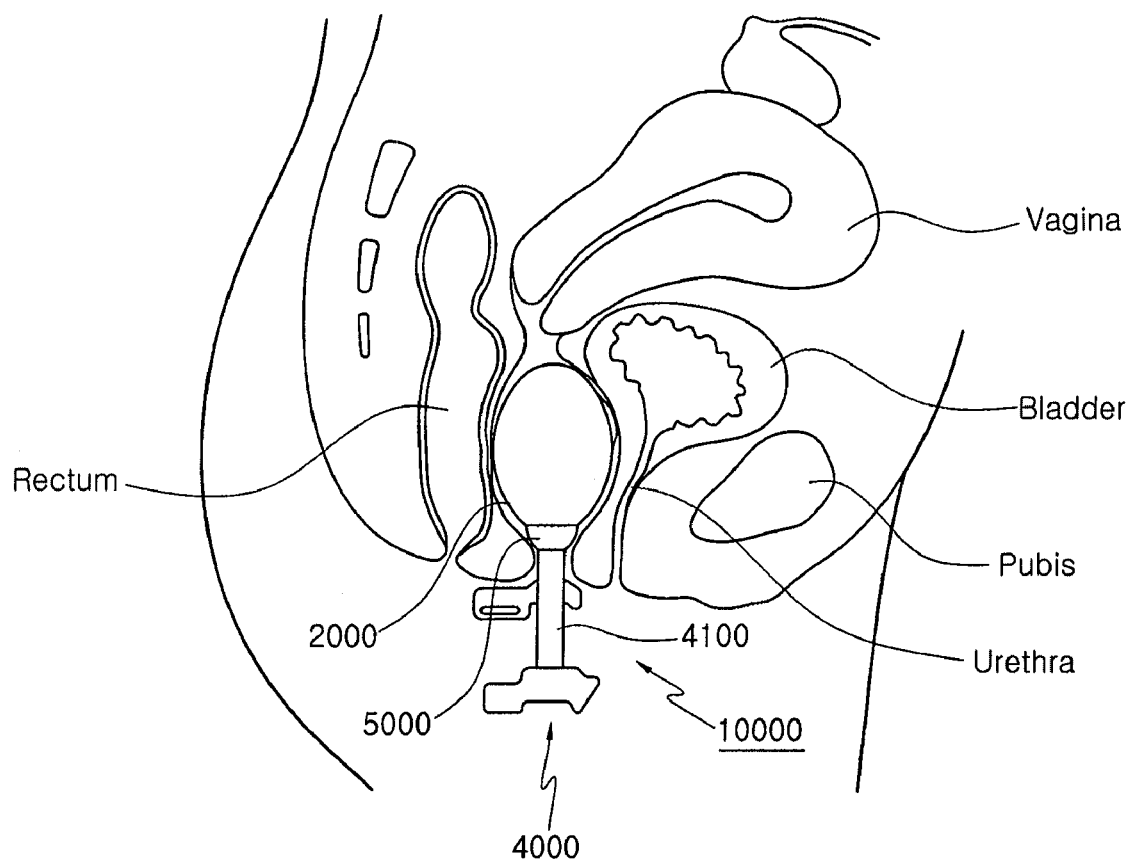
FIG. 6 is a schematic view showing an application of an apparatus for examining and curing urinary incontinence and exercising the pelvic floor muscles and vaginal muscles using bio-feedback, in accordance with an exemplary embodiment of the present invention

As shown in FIG. 5, when the various buttons for selecting functions (adjusting strength, start/finish) are pushed, power and a signal are transmitted to each component from the controller. Therefore, the motorized air pump, the air flow detection sensor, the pressure detection sensor, the stopwatch, the solenoid valve, and the spring air cylinder valve are operated according to each button to introduce or discharge the air, thereby determining a contraction/expansion strength, a contraction/expansion interval, or the like. Then, the PTC ceramic heater 1600, the vibration motor 1700, the image display means 8000, the sound generating means, etc., are operated to continuously perform examination, treatment, and bio-feedback exercise.

Further, FIGS. 7A to 7C illustrate an operational example for measuring a tension force of the pelvic floor muscles (vaginal muscles) and an internal volume of the vagina using an apparatus for examining and curing urinary incontinence and exercising the pelvic floor muscles and vaginal muscles using bio-feedback, in accordance with an exemplary embodiment of the present invention As shown in FIGS. 7A to 7C, the tension of the pelvic floor muscles (vaginal muscles) and the capacity of the vagina are determined by measuring the pressure and the air flux, and the measured values can be immediately recognized through the display device and the earphones. Before the measurement, since the vagina vibration massage is performed, the measurement can be more readily performed. In addition, measurement of the tension of the pelvic floor muscles (vaginal muscles) and the capacity of the vagina will be described in detail. First, in a state in which the user relaxes the pelvic floor muscles (vaginal muscles), air generated from the motorized air pump passes through the air flow detection sensor to maximally expand the insert expansion part inserted into the vagina. Then, the controller detects overload through the air flow detection sensor to stop operation of the motorized air pump and close the solenoid air injection valve. At this time, the pressure detection sensor measures the pressure of the insert expansion part 2000 to measure the tension of the pelvic floor muscles (vaginal muscles), and the air flow detection sensor measures the amount of air injected into the insert expansion part 2000 to measure the capacity (ml) of the vagina. Typically, the measurements are performed three times, and their maximum, minimum, and average values are output as image and sound and stored in a storage device of the controller 9000.

FIGS. 8A to 8C illustrate flowcharts showing an operational example for measuring a pressure and duration of contraction of the pelvic floor muscles (vaginal muscles) using an apparatus for examining and curing urinary incontinence and exercising the pelvic floor muscles and vaginal muscles using bio-feedback, in accordance with an exemplary embodiment of the present invention. This can be performed after measurement of the tension of the pelvic floor muscles (vaginal muscles) and the capacity of the vagina.

As shown in FIGS. 8A to 8C, measurement of the contraction pressure and duration of the pelvic floor muscles (vaginal muscles) will be described in detail. First, air pumped by the motorized air pump passes through the air flow detection sensor to expand the insert expansion part 2000 inserted into the vagina. At this time, the air flow detection sensor detects whether an appropriate amount of air, previously input to the controller 9000, is injected into the insert expansion part 2000. When the appropriate amount of air is injected, the controller 9000 stops the motorized air pump and closes the solenoid air injection valve. Then, while the user fully contracts the pelvic floor muscles (vaginal muscles) and holds, the pressure detection sensor measures the maximum contraction pressure (mmHg) of the pelvic floor muscles (vaginal muscles), and the stopwatch measures the time until the pressure value goes down under the maximum peak to measure the contraction duration (sec) of the pelvic floor muscles (vaginal muscles). Typically, the measurements are performed three times, and their maximum, minimum, and average values are output as image and sound and stored in the storage device of the controller 9000.

FIGS. 9A to 9C are flowcharts showing an operational example of exercising using bio-feedback for reinforcement of the pelvic floor muscles (vaginal muscles) using an apparatus for examining and curing urinary incontinence and exercising the pelvic floor muscles and vaginal muscles using bio-feedback, in accordance with an exemplary embodiment of the present invention.

As shown in FIGS. 9A to 9C, the apparatus of the present invention analyzes data stored in the controller 9000, for example, the tension and capacity, contraction pressure, contraction duration, and past exercise measurement values for the user, thereby enabling automatic selection of a mode appropriate to the user among ten strengths of exercise stored in the controller 9000, as well as manual selection. Operation of the apparatus will be described below. First, air pumped by the motorized air pump passes through the air flow detection sensor to expand the insert expansion part 2000 inserted into the vagina. At this time, the air flow detection sensor detects whether an appropriate amount of air, previously input to the controller 9000, is injected into the insert expansion part 2000 on the basis of exercise strength of each step of the user. When the appropriate amount of air is injected, the controller 9000 stops the motorized air pump and closes the solenoid air injection valve. When the user repeats contraction and relaxation of the pelvic floor muscles (vaginal muscles) according to instructions displayed on the image display means 8000 or output from the sound generating means 7000, the pressure detection sensor measures the contraction pressure of the pelvic floor muscles (vaginal muscles) using the insert expansion part 2000 inserted into the vagina. In addition, the controller 9000 may display instructions or guidance on the image display means 8000 in the form of a bar graph, numbers, or animation. In addition, the instructions or guidance may be output through the sound generating means 7000 as a voice or melody, or through the vibration motor 1700 installed in the insert frame 1000 as vibrations. When the user selects a light exercise mode, the solenoid air cylinder valve is opened to operate the spring air cylinder, thereby distributing the pressure of the insert expansion part 2000.

As described above, the controller 9000, the motorized air pump, the air flow detection sensor, the pressure detection sensor, the spring air cylinder, the solenoid air injection valve, the air tank, etc., may be installed in a single main box and controlled by switches to allow the user to readily use the apparatus by herself.

INDUSTRIAL APPLICABILITY

As can be seen from the foregoing, a single compact apparatus in accordance with the present invention includes four measurement functions, four treatment functions, and four scientific and precise pelvic floor muscle (vaginal muscle) reinforcement exercises, enabling convenient, easy and safe self-examination and treatment of urinary incontinence.

In addition, it is possible for a user to readily treat urinary incontinence by selectively adapting physical therapy or behavior therapy.

Further, it is possible to readily perform examination of urinary incontinence.

Furthermore, filler and so on are formed of a material emitting far infrared rays and anions to enhance treatment.

In addition, an insertion depth adjustment part is provided to increase applicability to different sizes of vagina and different treatment positions.

Further, a heater and a vibration motor are provided to simultaneously perform thermotherapy and vibration massage treatment.

Furthermore, it is possible for a user to check a treatment state by image and sound.

In addition, it is possible to provide music therapy as well.

Further, since a controller can perform smooth control, it is possible to readily use the apparatus without an expert.

The invention claimed is:

1. An apparatus for examining and curing urinary incontinence and exercising the pelvic floor muscles and vaginal muscles using bio-feedback, comprising:
   an insert expansion part;
   an insert frame, a portion of which is accommodated in the insert expansion part, extending in its longitudinal direction;
   a fixing means for fixing the insert expansion part to the insert frame;
   an air supply source connected to the insert expansion part and supplying air thereinto;
   an air supply path disposed between the air supply source and the insert expansion part; and
   a valve installed at the air supply path,
   wherein the air supply path comprises a spring air cylinder connected thereto, and a controller for controlling the spring air cylinder, and wherein the spring air cylinder is spaced from the air supply source and configured to distribute a pressure of the insert expansion part.

2. The apparatus for examining and curing urinary incontinence and exercising the pelvic floor muscles and vaginal muscles using bio-feedback according to claim 1, wherein the insert expansion part or the air supply path comprises a pressure detection sensor, a controller for receiving a signal from the pressure detection sensor and processing the signal, and an expression part connected to the controller.

3. The apparatus for examining and curing urinary incontinence and exercising the pelvic floor muscles and vaginal muscles using bio-feedback according to claim 2, wherein the expression part is a sound generating means or an image display means.

4. The apparatus for examining and curing urinary incontinence and exercising the pelvic floor muscles and vaginal muscles using bio-feedback according to claim 1, wherein the air supply path comprises an air flow detection sensor, a controller for receiving a signal from the air flow detection sensor and processing the signal, and an expression part connected to the controller.

5. The apparatus for examining and curing urinary incontinence and exercising the pelvic floor muscles and vaginal muscles using bio-feedback according to claim 1, wherein the insert expansion part is formed of an elastic member containing filler.

6. The apparatus for examining and curing urinary incontinence and exercising the pelvic floor muscles and vaginal muscles using bio-feedback according to claim 5, wherein the elastic member is formed of rubber.

7. The apparatus for examining and curing urinary incontinence and exercising the pelvic floor muscles and vaginal muscles using bio-feedback according to claim 6, wherein front and rear ends of the elastic member of the insert expansion part have a larger thickness than an intermediate part.

8. The apparatus for examining and curing urinary incontinence and exercising the pelvic floor muscles and vaginal muscles using bio-feedback according to claim 1, wherein, when viewed from the front, the insert expansion part has an aspect ratio of 1:1.2~1:2.5 on expansion.

9. The apparatus for examining and curing urinary incontinence and exercising the pelvic floor muscles and vaginal muscles using bio-feedback according to claim 1, wherein, when viewed from the front, the insert expansion part has a projection part formed at its upper part.

10. The apparatus for examining and curing urinary incontinence and exercising the pelvic floor muscles and vaginal muscles using bio-feedback according to claim 1, wherein the insert expansion part has an expansion support piece installed at its front end to be securely engaged with the insert frame.

11. The apparatus for examining and curing urinary incontinence and exercising the pelvic floor muscles and vaginal muscles using bio-feedback according to claim 1, wherein the insert expansion part has a fixing piece extending from its rear end.

12. The apparatus for examining and curing urinary incontinence and exercising the pelvic floor muscles and vaginal muscles using bio-feedback according to claim 1, wherein the insert frame has a streamlined insertion guide piece in contact with the insert expansion part at its front end.

13. The apparatus for examining and curing urinary incontinence and exercising the pelvic floor muscles and vaginal muscles using bio-feedback according to claim 1, wherein the insert frame has at least one of a PTC ceramic motor and a vibration motor.

14. The apparatus for examining and curing urinary incontinence and exercising the pelvic floor muscles and vaginal muscles using bio-feedback according to claim 1, wherein the insert frame, disposed outside the insert expansion part, comprises a handle.

15. The apparatus for examining and curing urinary incontinence and exercising the pelvic floor muscles and vaginal muscles using bio-feedback according to claim 1, wherein the controller comprises a stopwatch connected thereto.

16. An apparatus for examining and curing urinary incontinence and exercising the pelvic floor muscles and vaginal muscles using bio-feedback comprising:
   an insert expansion part;
   an insert frame, a portion of which is accommodated in the insert expansion part, extending in its longitudinal direction;
   a fixing means for fixing the insert expansion part to the insert frame;
   an air supply source connected to the insert expansion part and supplying air thereinto;
   an air supply path disposed between the air supply source and the insert expansion part;
   a valve installed at the air supply path;
   a pressure detection sensor installed at the insert expansion part or the air supply path;
   an air flow detection sensor installed at the air supply path;
   a controller connected to the valve, the pressure detection sensor, and the air flow detection sensor; and
   an expression part connected to the controller,
   wherein the air supply path comprises a spring air cylinder connected thereto, and a controller for controlling the spring air cylinder, and wherein the spring air cylinder is spaced from the air supply source and configured to distribute a pressure of the insert expansion part.

17. The apparatus for examining and curing urinary incontinence and exercising the pelvic floor muscles and vaginal muscles using bio-feedback according to claim 16, wherein the controller further comprises a data storage device.

* * * * *

UNITED STATES PATENT AND TRADEMARK OFFICE
CERTIFICATE OF CORRECTION

PATENT NO. : 8,360,954 B2  Page 1 of 1
APPLICATION NO. : 11/795882
DATED : January 29, 2013
INVENTOR(S) : Kyungil Kim It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1435 days.

Signed and Sealed this

First Day of September, 2015

Michelle K. Lee
*Director of the United States Patent and Trademark Office*